United States Patent
Doucet et al.

(10) Patent No.: US 10,094,782 B2
(45) Date of Patent: Oct. 9, 2018

(54) METHOD AND APPARATUS FOR FAST QUANTITATIVE ANALYSIS OF A MATERIAL BY LASER INDUCED BREAKDOWN SPECTROSCOPY (LIBS)

(71) Applicant: NATIONAL RESEARCH COUNCIL OF CANADA, Ottawa, Ontario (CA)

(72) Inventors: Francois Doucet, Laval (CA); Mohamad Sabsabi, Longueuil (CA); Lutfu-Celebi Ozcan, Montreal (CA); Jean-Francois Gravel, Quebec (CA); Francis Boismenu, Longueuil (CA)

(73) Assignee: National Research Council of Canada, Ottawa, Ontario (CA)

( * ) Notice: Subject to any disclaimer, the term of this patent is extended or adjusted under 35 U.S.C. 154(b) by 44 days.

(21) Appl. No.: 15/039,479

(22) PCT Filed: Nov. 26, 2014

(86) PCT No.: PCT/CA2014/000850
§ 371 (c)(1),
(2) Date: May 26, 2016

(87) PCT Pub. No.: WO2015/077867
PCT Pub. Date: Jun. 4, 2015

(65) Prior Publication Data
US 2017/0167982 A1    Jun. 15, 2017

Related U.S. Application Data

(60) Provisional application No. 61/909,043, filed on Nov. 26, 2013.

(51) Int. Cl.
*G01N 21/71* (2006.01)
*G01J 3/443* (2006.01)

(52) U.S. Cl.
CPC ............ *G01N 21/718* (2013.01); *G01J 3/443* (2013.01)

(58) Field of Classification Search
CPC ..................................................... G01N 21/718
(Continued)

(56) References Cited

U.S. PATENT DOCUMENTS

| 4,490,774 A | 12/1984 | Olson et al. |
| 4,499,520 A | 2/1985 | Cichanowski |

(Continued)

FOREIGN PATENT DOCUMENTS

| JP | H05140235 | 6/1993 |
| JP | 2000208358 | 7/2000 |

OTHER PUBLICATIONS

S.C. Tadolini, "Evaluation of Ultrasonic Measurement Systems for Bolt Load Determinations", Bureau of Mines, United States Department of the Interior, Denver, CO, 1990.

(Continued)

*Primary Examiner* — Abdullahi Nur
*Assistant Examiner* — Omar Nixon
(74) *Attorney, Agent, or Firm* — Kenneth Murphy

(57) ABSTRACT

The invention discloses an apparatus and method for use with Laser Induced Breakdown Spectroscopy (LIBS) systems that can be applied to the real time analysis of various materials. The invention, in one aspect, provides a layer-by-layer method to remove the undesired coating layer of a material in which a pulsed laser is coupled with high speed scanning optics. To prepare the surface for LIBS, (i) a pulsed laser beam is scanned over an area of the surface to ablate the surface coating layer; (ii) the laser parameters are changed (i.e. pulse duration is made smaller) and the area scanned again to polish the surface; and (iii) the laser parameters are changed again (i.e. pulse duration is made (Continued)

smaller yet again) and the area scanned again with spectrometric analysis of the plasma plume created by the laser (i.e. LIBS is performed).

20 Claims, 9 Drawing Sheets

(58) Field of Classification Search
 USPC ......................................................... 356/318
 See application file for complete search history.

(56) References Cited

U.S. PATENT DOCUMENTS

| | | | |
|---|---|---|---|
| 6,184,324 B1 | 2/2001 | Benz et al. | |
| 7,975,555 B2 | 7/2011 | Zhuang et al. | |
| 8,545,983 B2 | 10/2013 | Jiang et al. | |
| 8,743,451 B2 | 6/2014 | Farrand et al. | |
| 2006/0084957 A1* | 4/2006 | Delfyett | A61B 18/20 606/12 |
| 2006/0102343 A1* | 5/2006 | Skinner | E21B 7/15 166/250.1 |
| 2008/0105059 A1 | 5/2008 | Turnbull et al. | |
| 2011/0098942 A1 | 4/2011 | Turner | |
| 2013/0054156 A1 | 2/2013 | Hyett | |
| 2013/0100444 A1* | 4/2013 | Chesner | G01J 3/443 356/318 |
| 2013/0278930 A1* | 10/2013 | Liu | G01N 21/718 356/318 |
| 2014/0139608 A1* | 5/2014 | Rosario | B23K 26/0006 347/225 |

OTHER PUBLICATIONS

M. Hirao et al., "Contacless measurement of bolt axial stress using a shear wave electromagnetic acoustic transducer", NDT&E International, vol. 34, p. 179-183, 2001.

D.W. Greve et al., "An inductively coupled lamb wave transducer", IEEE Sensors Journal, vol. 27, No. 2, p. 295-301, 2007.

P. Zheng et al., "Crack detection with wireless inductively coupled transducers", in Proceedings of SPIE, San Diego, California, USA, 2008.

* cited by examiner

METHOD AND APPARATUS FOR FAST QUANTITATIVE ANALYSIS OF A MATERIAL BY LASER INDUCED BREAKDOWN SPECTROSCOPY (LIBS)

This application is a national phase entry of International Patent Application PCT/CA2014/000850 filed Nov. 26, 2014 and claims the benefit of U.S. Provisional Patent Application Ser. No. 61/909,043 filed Nov. 26, 2013, the entire contents of both of which are herein incorporated by reference.

FIELD OF THE INVENTION

This invention relates to a method and apparatus for preparing the surface of a material for a LIBS measurement. In particular, the invention is directed to a method and apparatus used to remove the undesired coating layer of a material in order to allow for an accurate and real time analysis of the bulk material using LIBS.

BACKGROUND OF THE INVENTION

LIBS is a well-known analytical technique for determining the constitution of a sample material that involves focusing a laser beam onto the surface of the sample with high enough power density (i.e. irradiance) to vaporize and ionize a small part of the sample material to produce a plasma or spark having an elemental composition representative of the material. Optical emissions from the plasma plume are collected with light collection optics, and the spectral distribution (i.e. intensity as a function of wavelength) of the collected optical emissions is analyzed in a spectrometer that produces information in electronic form describing the spectral distribution. Since atomic and molecular constituents of sample materials have characteristic optical emission spectra, the information produced by the spectrometer forms a fingerprint of the sample material, revealing the constituents of that part of the sample onto which the laser beam was focused. Plasmas and sparks are used interchangeably in this specification.

LIBS provides rapid, in situ, compositional analysis without touching the surface and is now employed in a wide range of applications such as, for example, the monitoring of active agents in pharmaceutical pills, the sorting of materials for recycling, the analysis of soil to determine its impurities and fertilizer content, and the determination of the composition of molten metallic alloys. The major challenge for these industries is increasing productivity, reducing costs, and maximizing benefits from existing equipment.

The elimination of sample preparation allowing rapid and direct analysis is generally extolled as an advantage of LIBS, especially for quantitative analysis. Material surfaces, however, generally comprise an oxide coating layer or a coating layer containing nitrate, slag, paint, oil, etc. that is not representative of the bulk material to be analysed. To use LIBS to analyse the bulk material, it is first necessary to remove the coating layer. Prior art methods are based on site-by-site analysis involving mechanically cutting or boring a hole into the material at one site using a mechanical drill or using a laser to ablate or clean the layer and expose the bulk material beneath, and then performing the LIBS analysis (see *Laser cleaning in conservation of stone, metal, and painted: state of the art and new insights on the use of the Nd:YAG lasers*, S. Siano et al., Appl. Phys. A (2012) 106:419-446). The site-by-site method has a number of problems that make representative sampling of the bulk material difficult and prevents one from realizing real-time analysis using LIBS.

For example, the energy distribution within the laser beam (typically a near Gaussian mode in many laser systems) used to clean or ablate the coating layer produces cone-shaped craters with non-negligible edge contribution to the ablated mass. The plasma produced by the laser also interacts with the wall of the crater and induces some mixing of material, which complicates the analysis by LIBS and impacts analytical precision and accuracy, in particular in the region close to an interface. Another problem is the limited thickness of the ablated mass by the laser pulses in the nanosecond regime which is in the order of a few tens of nanometers on, for example, metals. Although appropriate to use for cleaning/ablating coating layers having a thickness of a few micrometers, such methods cannot be used for coating layers having a thickness of a few hundred of micrometers or more due to the time required which prevents one from doing a fast analysis by LIBS. Lack of or poor sensitivity as compared to other analytical schemes is also a problem with using LIBS in this context. In fact, the large background emission (continuum radiation) of the hot laser-induced plasmas can mask and reduce the signal-to-noise ratios of the atomic emission signal from the analyte species, resulting in a lack of or poor sensitivity.

Several solutions have been proposed to remedy existing problems. In *Vadillo and Laserna* (J. Anal. At. Spectrometry, vol. 12, 1997, p. 859), it was proposed to improve the depth resolution of LIBS measurements by using a simple two-lens telescope combined with a pinhole mask to generate a collimated output of a XeCl excimer laser, resulting in a flat energy profile. Beam masking was also proposed to attenuate the shot energy and to eliminate the peripheral irregularity of the beam profile (see Kanicky et al., Fresenius J. Anal. Chem., vol. 336, 2000, p. 228). In US patent application publication no. 20030016353A1, an approach was proposed based on alternating a burst of shots for ablation and second burst focused in the center of the first burst for sampling. This approach, however, deals with depth profilometry at one position and cannot be applied for scanning the surface.

The above-mentioned approaches have failed, among others, to eliminate the interaction between the laser and the wall of the crater. Furthermore, these approaches can only be used for one position and for layers in the order of a few micrometers, which is a problem for samples or materials having non-homogenous or heterogeneous compositions due to difficulties in obtaining representative samples.

Thus, there remains a need for an improved method of removing the coating layer of a sample in order to allow for an accurate analysis of the bulk material realized in real-time using LIBS.

SUMMARY OF THE INVENTION

Briefly, the present invention provides a method and apparatus for preparing the surface of a material for a LIBS measurement.

The present invention also provides a method and apparatus for preparing the surface of a material for a LIBS measurement by removing or ablating the surface coating layer not representative of the bulk material in a very short of time using a special combination of variable duration laser pulses for ablation.

There is further provided a method and apparatus for cleaning the surface coating layer by variable pulse duration laser from undesired material not representative of the bulk, preparing that surface for analysis and measuring the evolution of concentration as a function of depth to achieve more accurate measurements than classical instrumentation, without sample preparation.

Specifically, the proposed invention is based on a layer-by-layer approach in which a pulsed laser is coupled with high speed scanning optics. To prepare the surface for LIBS, a pulsed laser beam is scanned over an area of the surface to ablate the surface coating layer. Once the surface coating layer is ablated in that area, the laser parameters are changed (i.e. pulse length or duration are made smaller) and the area scanned again to polish the surface. Once the area is polished, the laser parameters are changed again (i.e. pulse duration changed to intermediate pulse duration between the first and second pulse durations) and the area scanned again with spectrometric analysis of the plasma plume created by the laser (i.e. LIBS is performed).

More specifically, there is provided a method or process for analyzing bulk material by LIBS, the method or process comprising:

(a) scanning a surface layer of a bulk material to ablate said layer with a pulsed laser beam scanned over the area at a first laser beam regime comprising a first pulse duration;

(b) polishing the ablated surface with a pulsed laser beam scanned over the ablated area at a second laser beam regime comprising a second pulse duration shorter than the first pulse duration; and, (c) scanning the polished surface with a pulsed laser beam within the polished area at a third laser beam regime comprising a third pulse duration of intermediate pulse duration between the first and the second pulse duration to create a plasma plume of the bulk material having optical emissions that are detected by an optical device. Intermediate pulse duration means that the third pulse duration has a pulse duration smaller than the first pulse duration and larger than the second pulse duration.

The present invention features three different regimes of ablation using the same laser for preparation of the surface of a material. The first regime for cleaning or ablating produces a reproducible and controlled ablation that removes the undesired coating layer at a longer pulse duration (few hundreds of ns), followed by a second regime using pulses of shorter duration (few nanosecond pulses) to polish that surface from any residual coating and giving the material a smooth surface which doesn't lead to repeated oxidation. The third regime for analysis scans inside the cleaned area with overlapped spots in order to avoid the edges of the cleaned area. The third regime probe, collinear with the first, has a smaller sampling area and intermediate pulse duration in between that of the first and second pulse durations to allow generation of low background analytical plasma. The plasma emission is then collected and separated in an optical spectrometer.

The present invention further provides a method of analyzing materials using LIBS, comprising directing a first burst of ablation laser pulses (pulse with hundred of ns) in a first beam at a sample to clean and remove the undesired coating layer and to form an ablation surface according to a pattern with successive overlapped pulses with a bottom and a wall; directing a second burst with shorter laser pulses (few ns), low energy and high repetition rate to remove the residual coating layer, smoothening or polishing the surface and preparing it for the burst of analysis. Directing a third beam with intermediate laser pulses (few tens of ns) in a second beam to scan a smaller width than said first beam at the bottom of said area so as to create a plasma that emits radiation representative of a component in the sample without significant contribution from the wall of the ablation crater, measuring the intensity of radiation from said plasma; determining the concentration of said selected component in said material from the intensity of said radiation; and evaluating the depth at which said plasma is created. The above steps are preferably repeated in order to determine the evolution of concentration of the selected component as a function of depth.

Many laser systems produce a near-Gaussian energy distribution within the laser beam, which limits the depth resolution achievable with the LIBS technique as it produces cone-shaped craters with a non-negligible peripheral contribution to the ablated mass. The present invention allows one to obtain a more homogenous ablation by using high quality beam distribution. The ablation depth is controlled using a given number of laser shots or laser passes. The invention also allows one to perform an analysis of the surface at the bottom of the ablated zone, without any contribution from the crater wall and at constant fluence on the target allowing for reproducible measurements.

In another aspect of the invention, there is provided an apparatus for depth spectroscopic analysis of a material, comprising:

an energy source for generating pulses of energy in the form of a first laser beam of predetermined pulse duration for ablation of the surface layer of the material;

an energy source for generating pulses of energy in the form of a second laser beam of predetermined pulse duration, said second laser beam having a pulse duration less than said first laser beam; and, an energy source for generating pulses of energy in the form of a third beam of predetermined pulses duration, said third beam having intermediate pulse duration, to form a plasma emitting radiation representative of a selected component present in said material.

In another aspect of this invention, there is provided an apparatus for depth spectroscopic analysis of heterogeneous materials, comprising an energy source for generating pulses of energy in the form of a first beam of predetermined laser pulses duration appropriate for aggressive ablation for removal of undesired materials on a sample by a pattern of several passes with overlapped laser shots to cause ablation thereof and thereby forming a sufficiently large crater with a bottom and a wall; an energy source for generating a burst of pulses in a second beam of laser light, said second beam having a pulses duration less than said first beam and being directed at the bottom of said crater so as to smooth the surface and remove the residual coating and third beam of laser light with intermediate pulse duration to form a plasma emitting radiation representative of a selected component present in said material without significant contribution from the wall of the crater; a detector for measuring the intensity of radiation of said selected component at different depths of crater; and a depth profile evaluator for determining the depth of the crater for each radiation intensity measurement.

The energy sources can be one, two or three lasers disposed such that their optical paths are substantially collinear. A small deviation from collinearity is acceptable.

The measuring device, e.g. a spectrometer, is preferably disposed substantially collinearly with the optical path of the laser beams.

This invention also enhances the sensitivity and the reproducibility of the LIBS technique by using high repetition long pulse duration laser-induced plasmas with low background continuum.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which.

DETAILED DESCRIPTION OF THE EMBODIMENTS OF THE INVENTION

Figure 1:
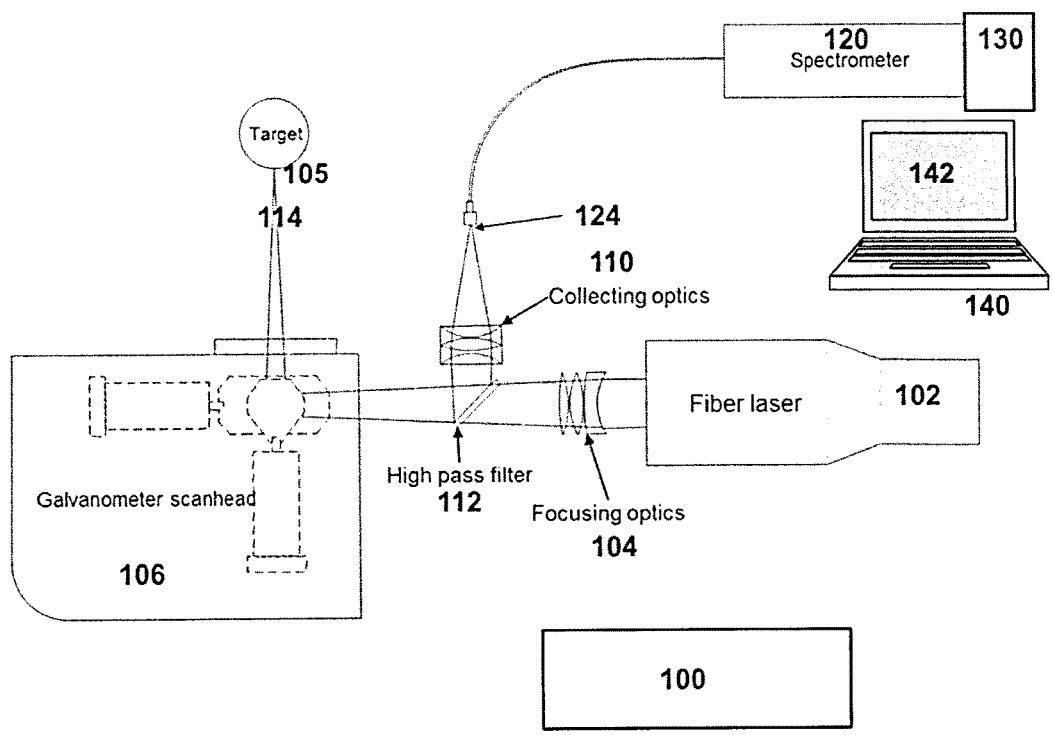
FIG. 1 illustrates a schematic diagram of a LIBS apparatus according to an embodiment of the invention.

FIG. 1 shows a schematic overview of a LIBS apparatus 100 according to one embodiment of the present invention. The individual components shown in outline or designated by blocks in these figures are all well-known in the LIBS arts, and their specific construction and operation are not critical to the operation or best mode for carrying out the present invention. The apparatus 100 generally includes a pulsed fiber laser 102, a galvanometer 106, a high pass filter 112, a spectrometer 120 and a system computer 140. The apparatus 100 is configured to generate laser pulses from the fiber pulsed laser 102. The laser pulses are focused onto a sample 105 with a lens 104 to produce a plasma plume 114 of the sample 105. The galvanometer scan head 106 is electrically coupled with the system computer 140 for sending a displacement error signal to automatically correct positioning of the sample 105 during an ablating process as described further below. That galvanometer can be programmed to scan a given surface according to a desired shape on the sample 105. The apparatus 100 can include a system frame for housing the various components described herein. The system frame can include an air filter for filtering contaminants produced during the ablating process.

The pulsed laser 102 in an exemplary embodiment comprises a fiber pulsed laser for generating energy in the near infrared region of the electromagnetic spectrum with a wavelength of 1064 nm. The pulse duration for the analysis is few tens of ns for generating a laser beam with a power density that can exceed one GW/cm$^2$ at a focal point or ablation impact point. The laser 102 can have a repetition rate of approximately 1 MHz or alternately lower than 10 Hz in some embodiments. Alternatively, the pulse duration can vary from few ns to hundreds of nanoseconds. The lens 104 comprises a beam expander and an objective lens used to focus the laser beam on a surface of the sample site 105. The laser beam can be focused to a spot size of approximately 10-100 micrometers on the sample site 105 according to the desired regime of ablation. In an exemplary embodiment, the laser beam can be focused to a spot size of approximately 150-200 micrometers on the sample site 105.

A dichroic mirror 112 is used for directing the laser beam toward the sample site 105 and allows reflecting the light emitted by the plasma 114 to be directed to the entrance of optical fiber through the collecting optics 110. The fiber optic guides the light to a combination spectrometer and detector 120.

The galvanometer 106 allows the beam to scan a desired surface on the target 105 without the need of a complicated stage XY to move the sample. In one embodiment of the invention, the laser beam scans the surface according to the pattern shown in FIG. 2A for the first ablation regime and for the polishing regime according to the pattern shown in FIG. 2B. The horizontal scanning regime is characterized by the scanning speed Vx and horizontal scanning step Δx between two successive laser spots, which are related by the laser spot size, the scanned surface and the laser repetition rate, e.g. 25 000 Hz. The vertical scanning regime is characterized by the vertical step Δy between two successive lines. The tested scanning regimes are presented graphically in FIGS. 2A and 2B and representative parameters are given in Table 1.

TABLE 1

Example of Parameters for Scanning Regimes

| Parameters | (1) Ablating/Cleaning | (2) Polishing | (3) Analysis |
|---|---|---|---|
| Pulse duration (ns) | 200 | 9 | 30 |
| Pulse energy (µJ) | 800 | 40 | 160 |
| Laser frequency (Hz) | 25000 | 500000 | 50000 |
| Diameter of the scan (mm) | 2 | 2 | 1.8 |
| Scan speed (mm/s) | 200 | 7000 | 200 |
| Step between spot (µm) | 30 | 30 | 30 |
| Number of layers | 10 | 2 | 5 |

Depending on the speed of the focused beam on the sample, a person skilled in the art will choose a suitable stepping spot. In one embodiment, the galvanometer scan head 106 can have a translation rate of approximately 200 mm/s for the first ablation regime and 7000 mm/s for the polishing regime and 200 mm/s for the LIBS analysis.

While the laser beam is focused on the target 105, the system 120 is collecting the light and monitoring the oxygen line which tags and detects the presence of oxide. Once the oxygen line is not detected or lower than the limit of the detection of oxygen by the detector 130, the system 140 indicates to the fiber laser 102 to switch to a shorter pulse duration for polishing the surface and smoothing it from residual oxide or particles from the previous first ablation regime and so on, then the laser beam scans the surface for the third LIBS analysis regime. The third regime devoted to analysis is shown in greater detail in step D of FIG. 8.

The spectrometer 120 in FIG. 1 collects electromagnetic information from the plasma plume 114. The spectrometer 120 can be monochromator or polychromator. The electromagnetic information includes spectral information identifying an elemental composition of the sample site 105. A spectral range for the spectrometer 120 can be chosen to suit different applications. In an exemplary embodiment the spectral range can be approximately 25 nm for observing a portion of the electromagnetic wavelength range. Alternatively, the spectrometer 120 can detect electromagnetic radiation in a range of 185 to 930 nm. The light emitted by the plasma plume is directed to the High pass filter 112 through the galvanometer scan head 106 following sufficiently collinear with the light pass for plasma generation. The High pass filter 112 reflects the light to the collecting optics 110 which focus the light to the entrance of fiber cable 124 guiding the light to the spectrometer 120. The spectrometer 120 reflects the light to a grating that disperses the plasma light. At the exit of the spectrometer 120, an intensified charge coupled device (ICCD) or detector 130 is coupled with the spectrometer 120 for detecting the dispersed plasma light. The detector 130 provides the detected plasma light to the system computer 140. The system computer 140 generates spectral information from the emitted plasma light of the laser plume 114. The spectral information includes intensity data representing elemental information and composition of the sample site 105. The spectral information can be produced on a display 142.

The detector 130 provides increased resolution and greater selectivity of the spectral information. The detector 130 includes a micro channel image intensifier plate. The intensifier plate is preferably gated during period of time when the plasma plume 114 emits characteristic atomic emission lines of the elements. This period coincides with an optimum plume luminance period. This period follows emission of continuum radiation. Continuum radiation lacks useful specific species or elemental information.

In one embodiment, a delay generator (not shown) can be included to provide gating of the detector 130 to allow temporal resolution of the detector 130 response time. Alternative embodiments of the detector 130 can include a detector other than an ICCD, for example a suitable charge coupled device (CCD) or suitable photomultiplier. Accuracy of the spectrometer 120 and detector 130 in one embodiment can generate compositional data in the range of 30 ppm or less. Alternatively, the accuracy can be in the range of a few %. In another embodiment, the accuracy can be in the range of 1%. Also in another embodiment the polychromater can be an Echelle spectrometer or a Pachen Runge spectrometer that can be coupled to several linear CCD covering the whole spectrum 170-900 or some portion of the spectrum of interest depending the application.

The system computer 140 can include application software and a controller in the system computer 140 for providing synchronization of the laser 102, spectrometer 120, detector 130, galvanometer scan head 106. The galvanometer scan head 106 can be also any kind of optic device to move the laser beam onto the sample. The system computer 140 is electrically coupled with the laser 102, spectrometer 120, detector 130, galvanometer scan head 106 and the detector 130. The system computer 140 includes a display 142 for displaying spectral information. The system computer 140 can present the spectral data generated on the display 142. Alternatively, a separate personal computer can also be coupled with the system computer 140 for separately analyzing the spectral information. The system computer 140 can include a power controller to regulate power to all the apparatus 100 components and also sensor for safety.

The application software decodes the spectral information from the detector 130, facilitates analysis of the spectral information and generates composition information of the sample 105. The application software allows setting of certain parameters for performing the laser ablation of the sample site 105. A spot circle, square or any geometrical shape desired and adapted to the sample 105 can be set as a parameter and can be consistently and precisely maintained through the Galvanometer Head Scan 106 according to the different regime of laser ablation process described in further detail below. Alternatively, according to the application software decoding the information from the detector 130, a number of passes can be set as a parameter and can be consistently and precisely maintained through the laser ablation process. The spot size of the ablated area decreases depending on the regime of ablation whether for polishing or analysis. Keeping the laser 102 ablated area scanned spot precisely adjusted insures that the sample site 105 produces the plasma plume 114 with consistent optimum plasma plume.

Figure 2A:
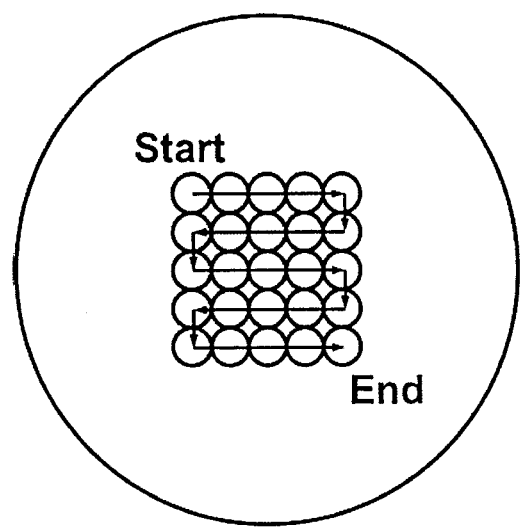
FIG. 2A illustrates a detail schematic diagram of the ablation regime for cleaning or ablating the surface according to an embodiment of the invention of a layer-by-layer scan pattern.
Figure 2B:
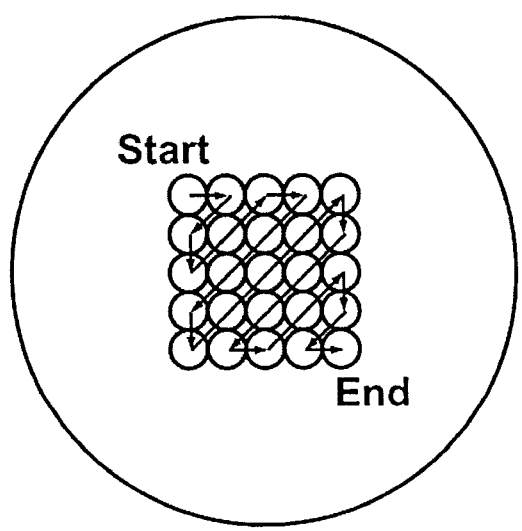
FIG. 2B illustrates a detail schematic diagram of the ablation regime for polishing the surface for analysis according to an embodiment of the invention of layer-by-layer scan pattern.
Figure 8:
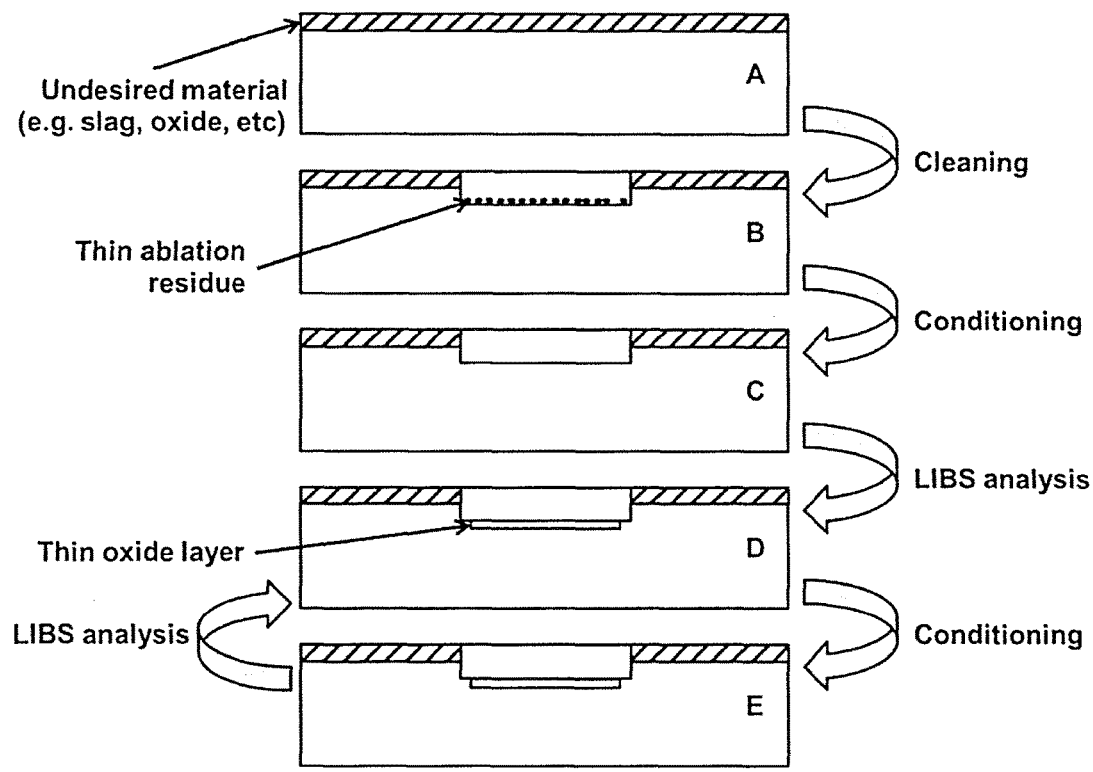
FIG. 8 illustrates a process flow diagram for a method of preparing the surface or ablating according to an embodiment of the present invention. It shows the ablation crater and the plasma formed using a conventional way at a given position and layer by layer according the embodiment of the invention.
Figure 9:
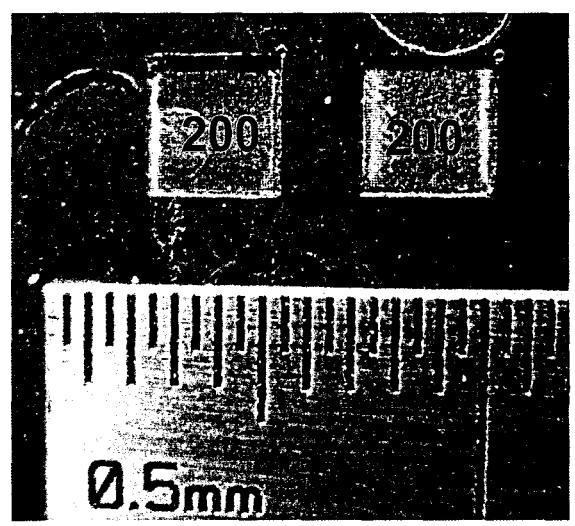
FIG. 9 illustrates the result of the first cleaning regime and the second polishing regime leaving a mirror-like surface exempt of undesired material and ready for accurate analysis.

As mentioned above, FIG. 2A shows representative graphical patterns for the first ablation regime. FIG. 2A shows the protocol for aggressive ablation and steps A to B of FIG. 8 show the protocol of the second polishing regime for removing the residual undesired material, polishing and preparing the surface for analysis. A spot prepared surface 200 obtained on steel sample by the protocol of the first ablation regime and the second polishing regime according to an embodiment of the present invention is shown on FIG. 9.

Figure 3:
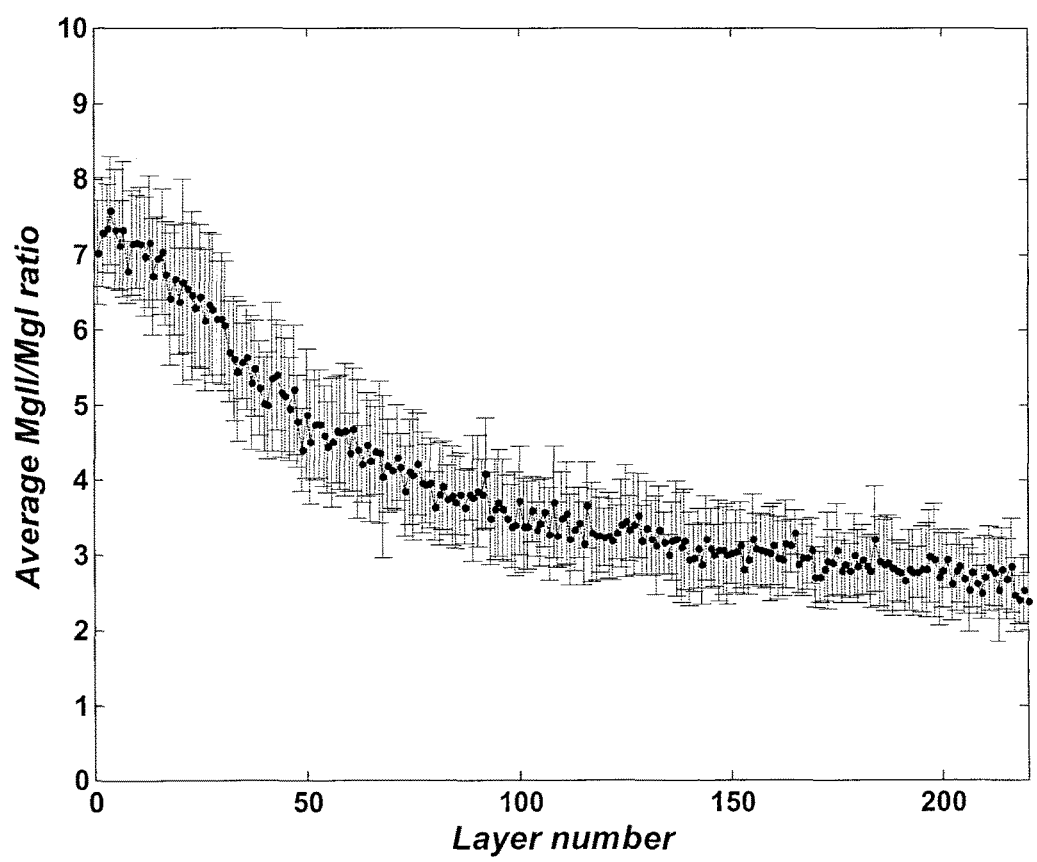
FIG. 3 illustrates the ratio of lines intensities of ionized and atomic line of magnesium according to a conventional LIBS (i.e. site-by-site) measurement at one position showing the variation of that ratio versus the number of shots on an Avicel/Lactose (1:1 ratio) and 0.5% magnesium stearate tablet, LIBS condition: Fluence: 100 J/cm$^2$; Irradience: 16 GW/cm$^2$, delay 0.5 μs, gate width 2 μs, each point are the average of 25 sites and error bar are the corresponding standard deviation for 250 shots per site.
Figure 4:
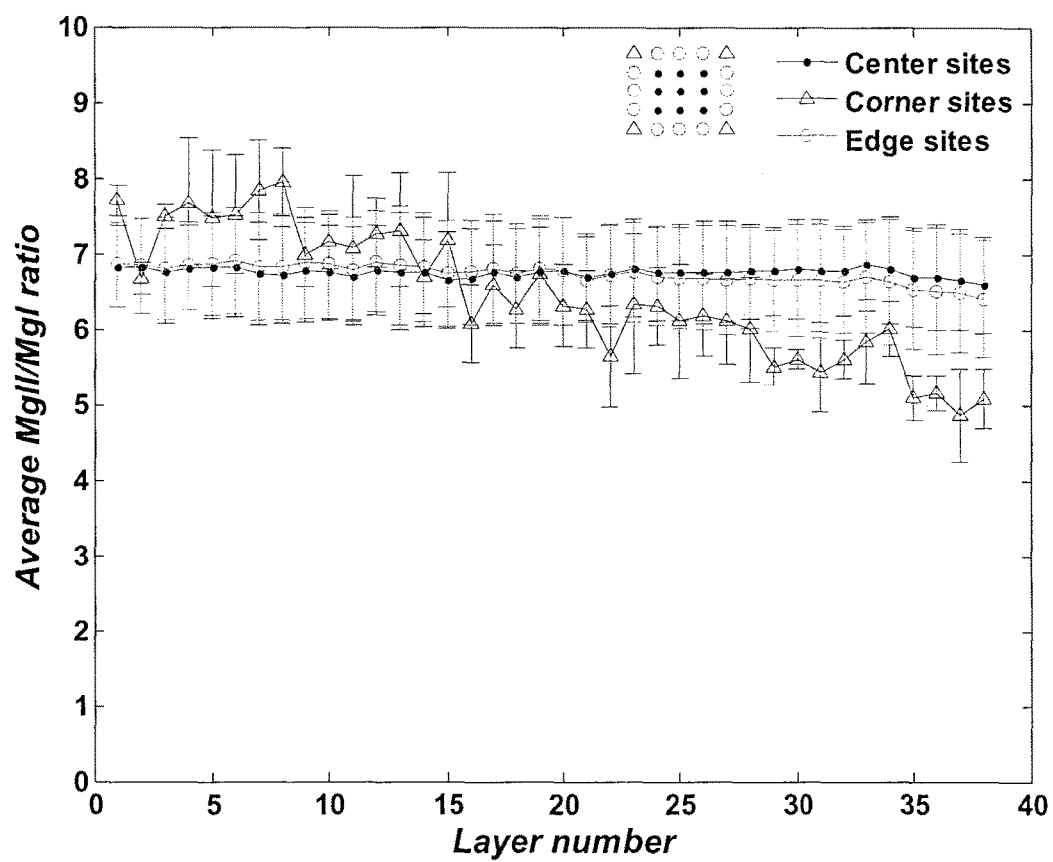
FIG. 4 illustrates the ratio of lines intensities of ionized and atomic line of magnesium versus the successive number of layer using layer-by-layer according to an embodiment of the present invention on an Avicel/Lactose (1:1 ratio) and 0.5% magnesium stearate tablet, LIBS condition: Fluence: 100 J/cm$^2$; Irradience: 16 GW/cm$^2$, delay 0.5 μs, gate width 2 μs, each point are the average of 25 shots per layer (i.e. 5×5 close packed spots) and error bar are the corresponding standard deviation for 25 shots per layer for 40 layers.
Figure 5A:
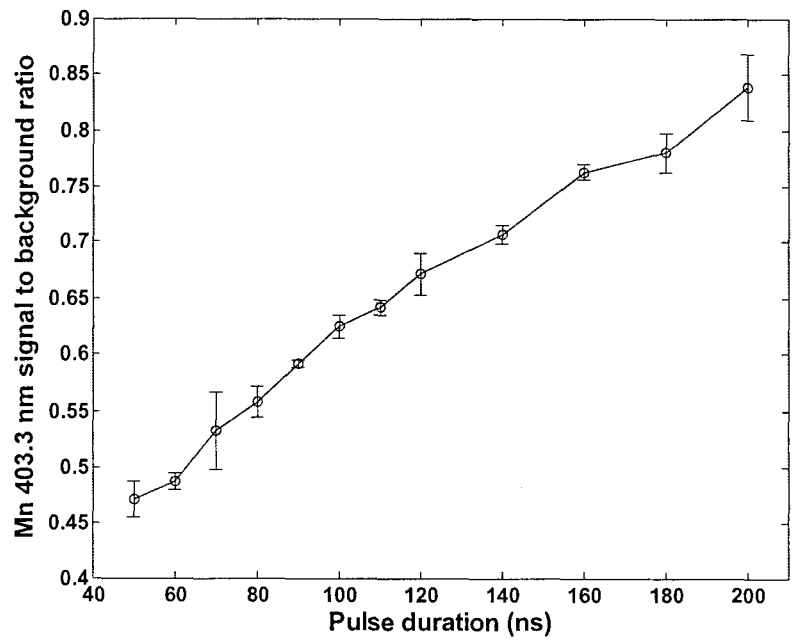
FIG. 5A Results of a non-gated LIBS experiment at constant average power (20 W), 800 ms integration time Aryelle 200 Echelle spectrometer equipped with an Andor Technology DH 334T-18F-E3 ICCD camera, 1 mm circle step 30 μm, scanner speed 200 mm/sec, SPI Laser G3 20 W.
Figure 5B:
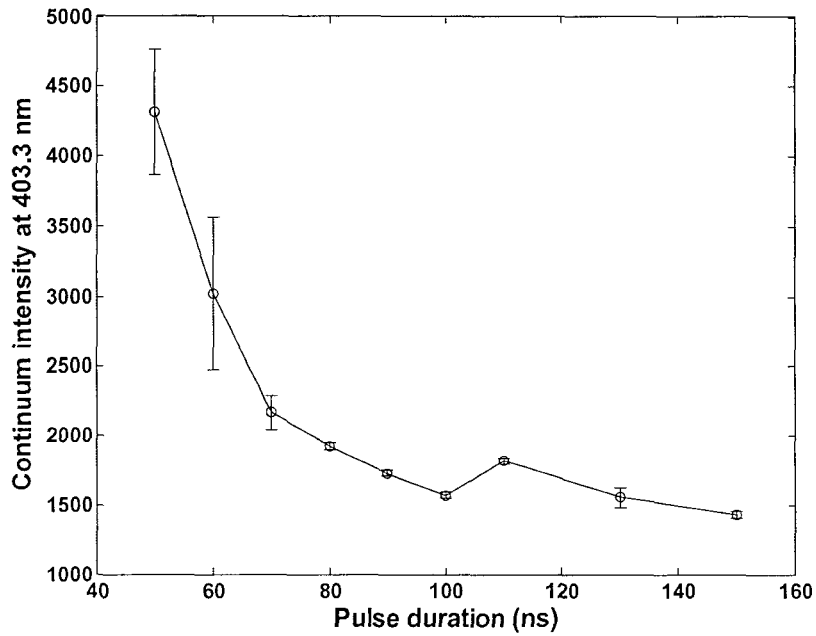
FIG. 5B Results of a non-gated LIBS experiment at constant average fluence (11 J/cm$^2$), 1 second integration time Aryelle 200 Echelle spectrometer equipped with an Andor Technology DH 334T-18F-E3 ICCD camera, 1 mm circle step 30 μm, scanner speed 200 mm/sec, SPI Laser G3 20 W.
Figure 6:
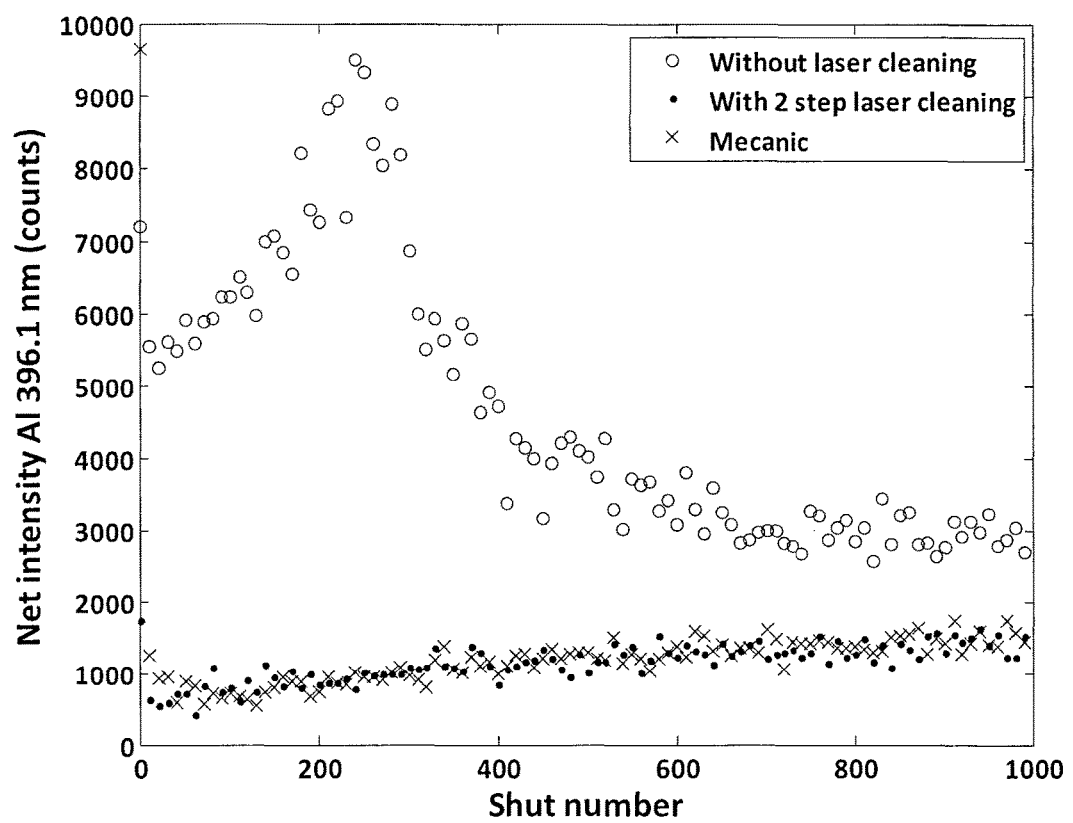
FIG. 6 Comparison of the evolution aluminium line intensity versus the shot number obtained at the same position (drilling) on steel sample having an oxide layer using conventional laser cleaning with the evolution obtained on the new 2 step layer-by-layer laser-cleaned surface and by mechanical removal of the oxide layer. Traditional LIBS experiment: 100 mJ on 800 μm (i.e. fluence of 80 J/cm$^2$; irradiance of 11 GW/cm$^2$) Spectrometer McPherson 2400 grooves/mm; blaze at 300 nm; slit of 30 μm; plasma image on the slit 1:2. Repetition rate 4 Hz (4 min 10 sec).
Figure 7:
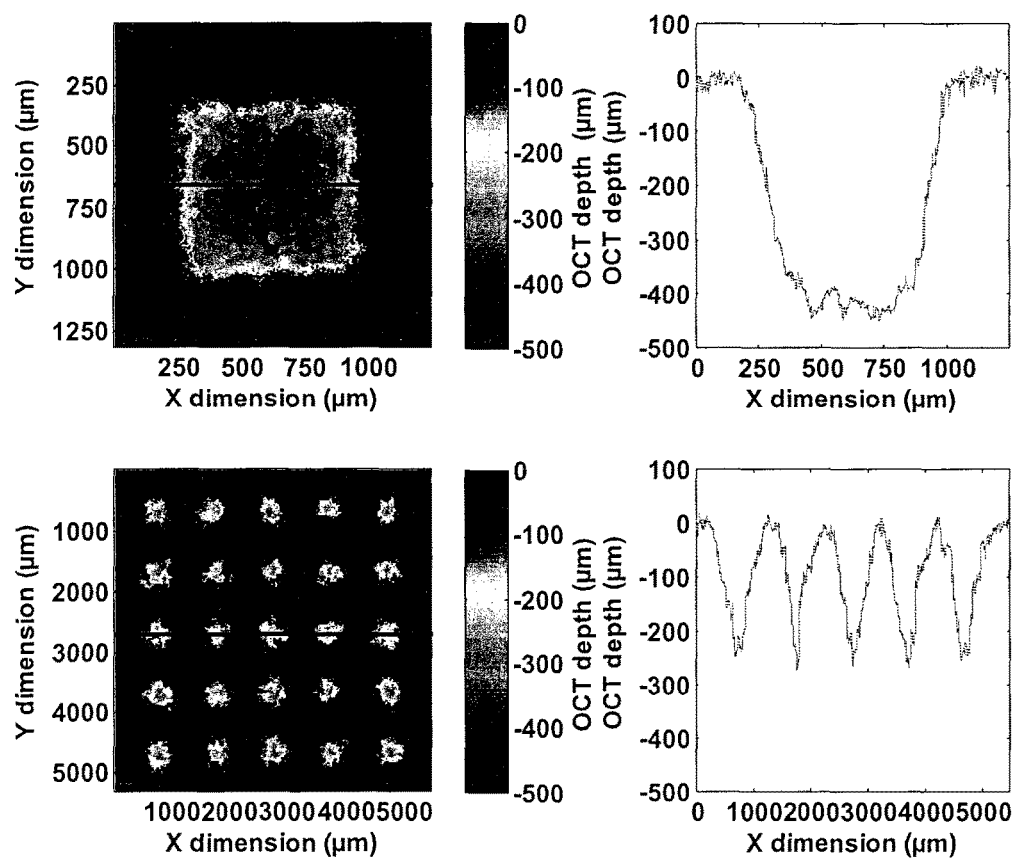
FIG. 7 Optical coherence tomography (OCT) images for a) and b) layer-by-layer and c) and d) site-by-site on an 0.5% o-carboxyphenyl phosphate Avicel/Lactose (1:1 ratio) and 0.5% magnesium stearate tablet, with following LIBS conditions: Fluence: 100 J/cm$^2$; Irradience: 16 GW/cm$^2$, delay 0.5 μs, gate width 2 μs, each point are the average of 25 shots per layer (i.e. 5×5 close packed spots) and error bar are the corresponding standard deviation for 25 shots per layer for 40 layers.

As mentioned above, for conventional LIBS analysis, the energy distribution within the laser beam (typically a near Gaussian mode in many laser systems) produces cone-shaped craters with non-negligible edge contribution to the ablated mass. The plasma produced by the laser also interacts with the wall of the crater and induces some mixing of material. This complicates the LIBS analysis and causes loss of analytical precision and accuracy, in particular in the interaction with wall of the crater which decreases the fluence on the sample site and affects the emission of the plasma. FIG. 3 shows the evolution of the ionic to atomic magnesium line intensity ratio against the layer number of the site-by-site sampling when using traditional LIBS analysis known in the prior art. The decrease of the ratio due to the decrease of the laser fluence on the target which affects the plasma emission and the interaction with the wall of the crater (instead of a constant signal) is clear seen. FIG. 4 illustrates the evolution of the ratio versus the layer number, specifically, the ionic to atomic magnesium line intensity ratio spectral information shows the stability of the laser-induced plasma temperature when avoiding analyzing the corner or edge of the sampled area. This allows selecting reproducible plasmas to be taken into account in the measurement and it shows clearly an advantage of the approach of the present invention.

Application of this invention is not limited to solid materials and can be used, for e.g, for the analysis of liquids (aqueous and other solutions) where more than a single phase is present, such as high temperature molten materials, for e.g. metals, metallurgical mattes, salts and glasses. This invention is also applicable to the preparation of the surface of materials in liquid phase. This invention can also be used for the analysis of both homogeneous and heterogeneous materials.

In the agriculture sector specifically, the invention can be used in various ways to determine the elemental analysis of a soil sample or to determine its PH in order to prepare a fertilization plan. One possibility is to analyse a prepared or non-prepared, heterogeneous or homogeneous, soil sample. These approaches depend on the analysis time available which is limited by the laser frequency. For e.g., it is possible to analyze each sample by using 25000 Hz fiber laser pulses by ablating layer by layer according to the embodiment of the present invention. This allows for an accurate sampling, reproducible measurements and obtaining results much faster than other analytical methods known in the art. The off-line determination by ICP, for e.g. requires sample preparation and analysis that takes one hour or more. Similarly to the analysis of soil, the present invention can be applied to the analysis of metallurgic powder.

In the metal recycling industry, the invention can be used to clean the surface of a metal from paint, fume, dust, oxide etc. and to prepare a clean surface representative of the bulk. By using a high repetition fiber laser rate of 20 kHz, one can clean the surface according to the embodiment of the present invention in less than a fraction of a second and carry out the accurate analysis representative of the bulk. Such analysis can be used for sorting the alloy according to its composition.

What has been described is an improved method and apparatus for preparing the surface of a material for LIBS analysis. The novel features will become apparent to those of skill in the art upon examination of the description. It should be understood, however, that while only certain features of the invention have been illustrated and described herein, many modifications and changes will occur to those skilled in the art. It is, therefore, to be understood that the appended claims are intended to cover all such modifications and changes and that the scope of the claims should not be limited by the embodiments, but should be given the broadest interpretation consistent with the wording of the claims and the specification as a whole.

The invention claimed is:

1. A method for analyzing bulk material by laser induced breakdown spectroscopy (LIBS), comprising:
    (a) scanning a surface layer of the bulk material to ablate said layer with a pulsed laser beam scanned over the area at a first laser beam regime comprising a first pulse duration;
    (b) polishing the ablated surface with a pulsed laser beam scanned over the ablated area at a second laser beam regime comprising a second pulse duration shorter than the first pulse duration; and,
    (c) scanning the polished surface with a pulsed laser beam within the polished area at a third laser beam regime comprising a third pulse duration of intermediate pulse duration between the first and the second pulse duration,
    to create a plasma plume of the bulk material having optical emissions that are detected by an optical device.

2. A method according to claim 1, wherein the ablated surface in step (a) is formed by a pattern of laser passes with successive overlapped pulses.

3. A method according to claim 1, wherein in step (a), a crater having a bottom and wall is formed.

4. A method according to claim 1, wherein in step (b), the second beam is directed at the bottom of the crater.

5. A method according to claim 1, wherein in step (c), the pulsed laser beam scans a smaller area than the pulsed laser beam in step (a).

6. A method according to claim 1, wherein in step (b), the pulsed laser beam scans a smaller area than the pulsed laser beam in step (a).

7. A method according to claim 1, wherein the material is heterogeneous.

8. A method according to claim 1, further comprising the step of measuring the intensity of radiation from the plasma.

9. A method according to claim 1, further comprising the step of measuring the concentration of a component of the material from the intensity of radiation from the plasma.

10. A method according to claim 1, further comprising the step of measuring the depth at which the plasma is created.

11. A method according to claim 1, wherein the optical device is disposed substantially collinearly with the optical path of the laser beams.

12. A method according to claim 1, wherein said bulk material is a soil sample.

13. A method according to claim 1, wherein said bulk material is a metal sample.

14. An apparatus for depth spectroscopic analysis of a material, comprising:

an energy source for generating pulses of energy in the form of a first laser beam of predetermined pulse duration for ablation of the surface layer of the material;

an energy source for generating pulses of energy in the form of a second laser beam of predetermined pulse duration, said second laser beam having a pulse duration less than said first laser beam; and, an energy source for generating pulses of energy in the form of a third beam of predetermined pulses duration, said third beam having intermediate pulse duration, to form a plasma emitting radiation representative of a selected component present in said material.

15. An apparatus according to claim 14, further comprising a detector for measuring the intensity of radiation of the selected component at different depths of crater.

16. An apparatus according to claim 14, further comprising a depth profile evaluator for determining the depth of the crater for each radiation intensity measurement.

17. An apparatus according to claim 14, wherein the energy sources can be one, two or three lasers disposed such that their optical paths are substantially collinear.

18. An apparatus according to claim 14, wherein the pulse duration of the first, second and third laser beams are about 200, 9, and 30 ns respectively.

19. An apparatus according to claim 14, further comprising a delay generator.

20. A method for analyzing bulk material by laser induced breakdown spectroscopy (LIBS), comprising the steps of:

(a) scanning a surface layer of the bulk material to ablate said layer with a pulsed laser beam scanned over an area;

(b) polishing the ablated surface with a pulsed laser beam scanned over the ablated area; and, (c) scanning the polished surface with a pulsed laser beam within the polished area with overlapped spots in order to avoid corner sites or edge sites of the scanned area.

\* \* \* \* \*